United States Patent [19]

Jones

[11] 4,238,486

[45] Dec. 9, 1980

[54] INDOLOBENZOXAZINES

[75] Inventor: James H. Jones, Blue Bell, Pa.

[73] Assignee: Merck & Co., Inc., Rahway, N.J.

[21] Appl. No.: 96,966

[22] Filed: Nov. 23, 1979

[51] Int. Cl.$^3$ .................. A61K 31/395; C07D 498/04
[52] U.S. Cl. .................... 424/248.4; 544/99; 260/326.13 R; 260/326.5 B
[58] Field of Search ...................... 544/90; 424/248.4

[56] References Cited

U.S. PATENT DOCUMENTS 3,968,111   7/1976   Bach et al. ...................... 424/261 X

OTHER PUBLICATIONS

Kornfeld et al., J. Am. Chem. Soc., vol. 78, pp. 3087–3114, (1956).
Bowman et al. (I), J. Chem. Soc., Perkin I, pp. 438–442, (1973).
Bowman et al. (II), J. Chem. Soc., Perkin I, pp. 760–766, (1973).
Chemical Abstracts, 9th Collective Subject Index, (vols. 76–85), 1972–1976, Hexanon-Iron, p. 19906CS, Am. Chem. Society, (1978).
Bach et al. II, J. Med. Chem., vol. 17, pp. 312–314, (1974).
Cassady et al., J. Med. Chem., vol. 17, pp. 300–307, (1974).
Floss et al., J. Pharm. Sci., vol. 62, 699 ff, (1973).
Meites et al., Vitamins and Hormones, vol. 30, pp. 165–221, (1972).
Rubin et al., Clin. Pharmacol. Ther., vol. 23, pp. 272 ff (1978).
Sehneider et al., Experientia, vol. 33, p. 1412 ff, (1977).
Von Stuz et al., Helv. Chim. Acta., vol. 55, 75 ff, (1972).
von Troxler et al., Helv. Chim. Acta, vol. 40, 2160 ff, (1956).

*Primary Examiner*—John D. Randolph
*Attorney, Agent, or Firm*—Daniel T. Szura; Harry E. Westlake, Jr.

[57] ABSTRACT

Indolobenzoxazines, their preparation and pharmaceutical use are disclosed.

37 Claims, No Drawings

INDOLOBENZOXAZINES

BACKGROUND OF THE INVENTION:

The present invention is concerned with indolobenzoxazines having antihypertensive protactin inhibiting, and anti-Parkinson activity.

The tetracyclic ergoline ring system is illustrated by the formula

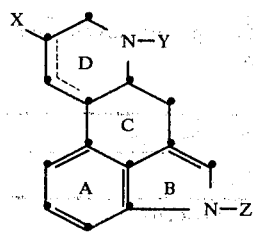

various dertivatives of the ergoline structure are known and have pharmaceutical activity [see e.g. Kornfeld et al., JACS 78,3087 (1956); Bach et al., J. Med. Chem. 17, 312 (1974); U.S. Pat. No. 3,968,111; Floss et al., J. Pharm. Sci. 62, 699 (1973); Cassady et al., J. Med. Chem. 17, 300 (1974)]

The compounds of the present invention are also tetracycles but are characterized by a benzoxazine D ring. The newly discovered bnezoxazines are illustrated by the formula

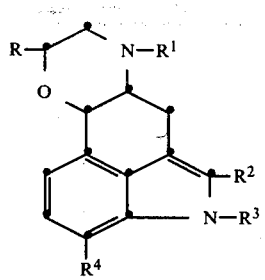

These compounds have pharmaceutical activity for example as antihypertensives, for prolactin inhibition, and as anti-Parkinson agents.

SUMMARY OF THE INVENTION

Indolobenzoxazines of the formula

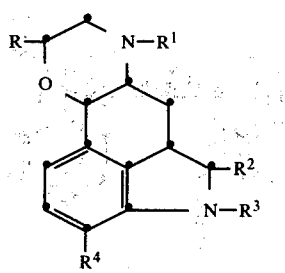

have been discovered, and their use as pharmacologically active agents.

DESCRIPTION OF PREFERRED EMBODIMENTS

An embodiment of the present invention are compounds of the formula

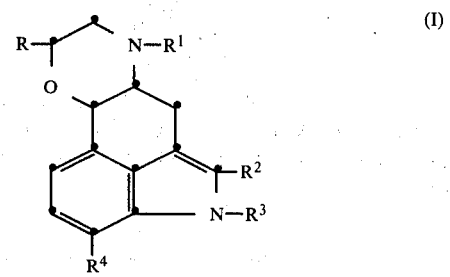

and pharmaceutically acceptable salts thereof wherein
R is H, alkyl or aryl,
$R^1$ is H, alkyl, aralkyl, alkenyl or cycloalkyl,
$R^2$ is H, halogen or alkyl,
$R^3$ is H, alkyl or aralkyl and
$R^4$ is H, halogen, alkyl, alkoxy or hydroxy.

The pharmaceutically acceptable salts of formula I are the salts with organic or inorganic acids. Suitable organic acids are carboxylic acids such as acetic acid, pamoric acid, citric acid, malic acid, maleic acid, butyri acid, succinic acid, lauric acid, lactoric acid, fumaric acid, pivalic acid, and oxalic acid and non-carboxylic acids such as isethionic acid, arylsulfonic acids, methanesulfonic acids and the like. Useful inorganic acids are $H_2SO_4$, phosphoric acid and the hydrohalides such as HCl and HBr.

These acid salts are ordinarily prepared by treating the appropriate Formula I free base with a suitable amount of acid using conventional procedures.

The alkyl groups may be branched or linear and may have up to 12 carbon atoms, with $C_1$-$C_6$ alkyl being preferred and $C_1$-$C_4$ being more preferred. $C_2H_5$ is a most preferred group.

The aryl groups may have up to 10 carbon atoms, with phenyl and substituted phenyl being preferred. The substituted phenyl group may be mono- or disubstituted, with the monosubstituted phenyls being preferred. The substituents include halogen, especially Cl and Br, $C_1$-$C_4$ alkyl such as t-butyl, butyl, ethyl and the like and especially $C_1$-$C_3$ alkyl e.g. $CH_3$ and $C_3H_7$, and $C_1$-$C_4$-alkoxy groups such as $CH_3O$—, sec-butoxy, ethoxy and the like.

The aralkyl groups include arylsubstituted-$C_1$-$C_4$ alkyls and preferably arylsubstituted $C_1$-$C_3$ alkyls. The aryl group may contain up to 10 carbon atoms and is preferably a phenyl group or substituted phenyl group of the type described above. Again the monosubstituted phenyl moiety is preferred especially halophenyl, $C_1$-$C_3$-alkoxy phenyl and $C_1$-$C_4$ alkylphenyl. Examples of phenylalkyl groups are benzyl, p-tolylethyl, $C_6H_5$—$C_4H_8$—,

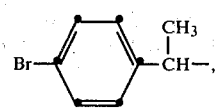

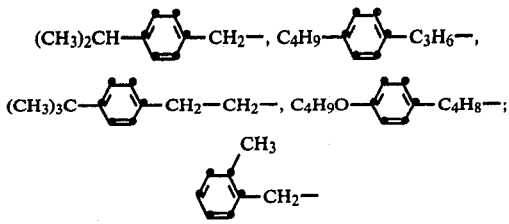

The cycloalkyl groups have up to 6 carbons and are exemplified by cyclopropyl, cyclohexyl, cyclobutyl, cyclopentyl

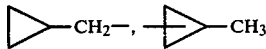

and the like. The C$_3$ or C$_4$ cycloalkyl groups are preferred, especially the cyclopropyl group.

The alkenyl groups may have up to 6 carbon atoms such as HC≡CH—(CH$_2$)$_4$—, CH$_2$=C(CH$_3$)—CH$_2$—, CH$_2$=C(CH$_3$)—, CH$_2$=CH—(CH$_2$)$_2$— and the like. The C$_3$ or C$_4$-alkenyl groups are preferred especially the H$_2$C=CH—CH$_2$— group.

Preferred compounds of formula I are those wherein
R is H, C$_1$-C$_6$ alkyl, phenyl, substituted phenyl,
R$^1$ is H, C$_1$-C$_6$ alkyl, alkenyl of up to 6 carbon atoms C$_3$-C$_6$ cycloalkyl, phen-C$_1$-C$_4$-alkyl or substituted phen-C$_1$-C$_4$-alkyl.
R$^2$ is H, Cl, Br or C$_1$-C$_6$ alkyl,
R$^3$ is H, C$_1$-C$_6$ alkyl, phen-C$_1$-C$_4$-alkyl or substituted phen-C$_1$-C$_4$-alkyl and
R$^4$ is H, Cl, Br, C$_1$-C$_6$ alkyl, hydroxy or C$_1$-C$_4$-alkoxy.

More preferred compounds of Formula I are those wherein
R is H, C$_1$-C$_4$ alkyl or monosubstituted phenyl wherein said substituent is halogen, C$_1$-C$_4$-alkyl or C$_1$-C$_4$ alkoxy,
R$^1$ is H, C$_1$-C$_4$ alkyl, C$_3$-C$_6$ cycloalkyl, C$_3$-C$_4$ alkenyl, monosubstituted phen-C$_1$-C$_4$-alkyl wherein said substituent is halogen, C$_1$-C$_4$ alkyl or C$_1$-C$_4$ alkoxy,
R$^2$ is H, Cl or Br,
R$^3$ is H, C$_1$-C$_3$ alkyl, monosubstituted phen-C$_1$-C$_4$-alkyl wherein said substituent is halogen, C$_1$-C$_4$ alkyl or C$_1$-C$_4$ alkoxy, and
R$^4$ is H, Cl, Br, C$_1$-C$_3$ alkoxy, hydroxy or CH$_3$;
preferred R$^1$ groups are H, C$_1$-C$_3$alkyl such as propyl or methyl, C$_3$-C$_4$ cycloalkyl such as

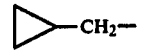

or cyclopropyl or C$_3$-C$_4$ alkenyl such as CH$_2$=CH—CH$_2$.

Compounds of the present invention are illustrated in the following table.

TABLE 1

| Compound | R | R$^1$ | R$^2$ | R$^3$ | R$^4$ |
|---|---|---|---|---|---|
| 1 | H | CH$_3$CH—CH$_2$—CH$_3$ | H | Cl—C$_6$H$_4$—CH$_2$ | OH |
| 2 | H | —CH(CH$_3$)$_2$ | Cl | H | Cl |
| 3 | H | CH$_3$ | Br | benzyl | Br |
| 4 | C$_6$H$_{13}$ | CH$_2$=CH—CH$_2$— | C(CH$_3$)$_2$ | CH(CH$_3$)$_2$ | OH |
| 5 | phenyl | H | C$_3$H$_7$ | C$_2$H$_5$ | C$_4$H$_9$—O |
| 6 | C$_2$H$_5$—O-phenyl | H | C$_4$H$_9$ | C$_3$H$_7$—O—C$_6$H$_4$—CH$_2$ | OH |
| 7 | p-tolyl | CH$_2$=CH(CH$_2$)$_3$— | H | C$_2$H$_5$—C$_6$H$_4$—(CH$_2$)$_4$ | CH$_3$O |
| 8 | (CH$_3$)$_3$C— | C$_2$H$_5$ | H | CH$_3$C$_6$H$_4$=CH$_2$— | CH(CH$_3$)$_2$—O |
| 9 | 2-bromophenyl | C$_4$H$_9$ | H | C$_3$H$_7$—O— | CH$_3$ |
| 10 | chlorophenyl | H | C$_2$H$_5$ | H | OH |
| 11 | naphthyl | cyclopropyl | C$_6$H$_{13}$ | H | Cl |
| 12 | H | cyclopentyl | Br | (Cl)$_2$—C$_6$H$_3$—CH$_2$ | H |
| 13 | H | CH$_2$=CH—CH$_2$ | Br | CH$_3$ | H |
| 14 | C$_2$H$_5$ | C$_2$H$_5$—O—C$_6$H$_5$—C$_2$H$_4$— | Cl | H | H |
| 15 | —C(CH$_3$)$_3$ | Br—C$_6$H$_5$—CH$_2$ | Cl | Br—C$_6$H$_4$—C$_2$H$_4$— | Br |
| 16 | H | Cl—C$_6$H$_5$—C$_3$H$_7$ | H | CH$_3$O | C$_5$H$_{11}$ |
| 17 | CH(CH$_3$)$_2$—C$_6$H$_4$— | H | H | (CH$_3$)$_2$CH—O | C$_2$H$_5$O |
| 18 | CH$_3$ | p-tolyl—C$_4$H$_8$ | C$_5$H$_{11}$ | benzyl | CH$_3$ |

The compounds of the present invention may be prepared by any covenient process. The following set of reaction equations indicates a useful scheme; tos stands for p-tolylsulfonyl.

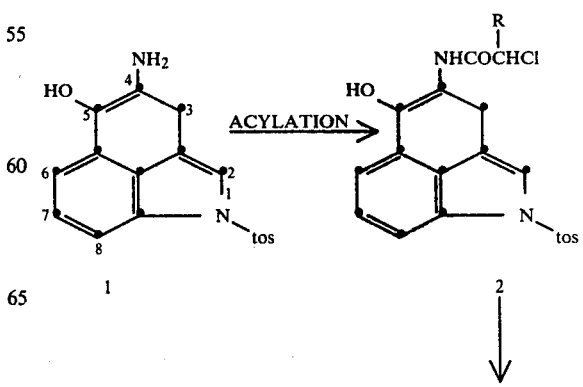

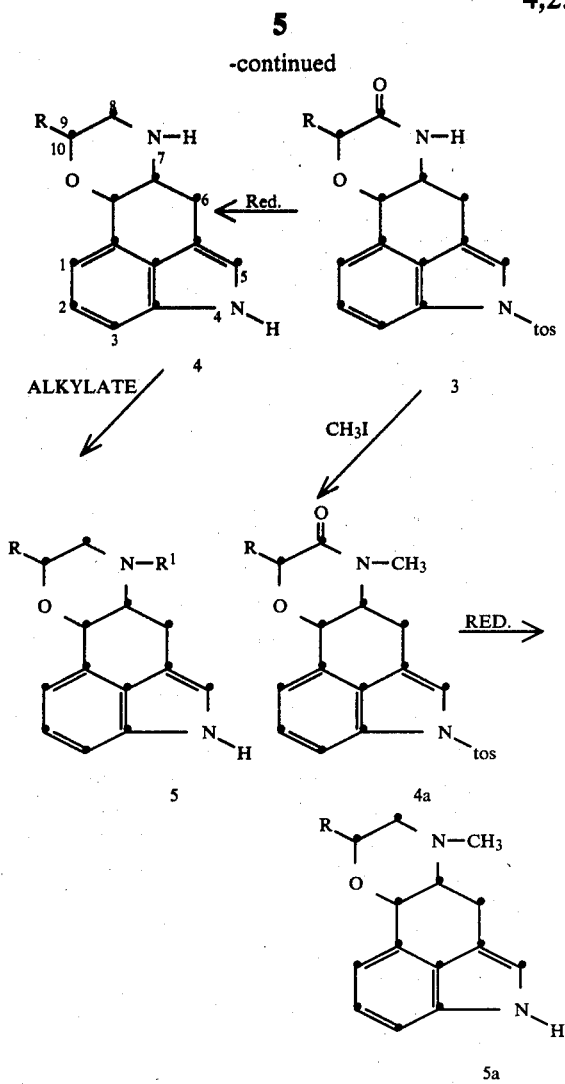

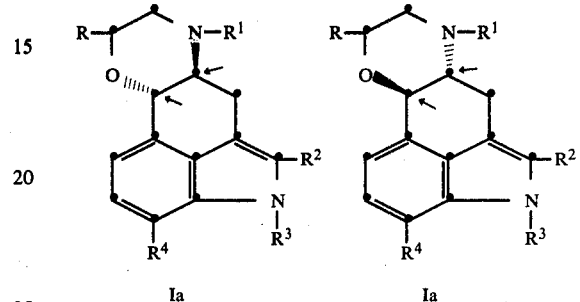

Known compound 1 [see Bowman et al., J.C.S. Perkin I, I, 438 (1973)] is acylated using a conventional procedure to produce the 4-acylamino derivative 2. Ring closure of compound 2 is effected by treating it with a strong base in a suitable solvent e.g. an aprotic solvent such as dimethylformamide (DMF). The tetracyclic indoloketobenzoxazine 3 may then be reduced using an appropriate agent e.g. lithium aluminum hydride (LAH) to yield the indolobenzoxazine 4. (The ring position numbering system is indicated in 4) This compound 4 is then reductively alkylated by using conventional alkylating agents and conditions, including reductive alkylation with an appropriate aldehyde to produce the 7-alkyl substituted compound 5, which is a compound of the present invention.

Where the 7-alkyl substituent is $CH_3$, the methyl group is first substituted on compound 3 by treatment with a strong base e.g. NaH and then with $CH_3I$. Compound 4a which is obtained is then reduced to obtain the 7-methyl substituted compound 5a.

The reaction scheme illustrates preparation of compounds of formula I where the R, $R^2$, $R^3$ and $R^4$ substituents are all H. Compounds of formula I where R, $R^2$, $R^3$ and $R^4$ are substituents other than H may be prepared using substantially the same scheme but using (a.) an appropriately substituted type 1 compound having $R^2$, $R^3$ and/or $R^4$ other than H, (b.) conventional procedures to directly substitute various groups at the 3, 4, 5 and/or 7 positions on a formula I compound which is partially substituted e.g. compound 4 or compound 5a or (c.) using an acylating agent in the reaction involving a type 1 compound which would provide an alkyl or aryl R substituent on ring closure. Reductive alkylation or other alkylation procedures provide various $R^1$ substituents at position 7.

A process for substituting a halogen (Br) in the type I compound is described in von Troxler et al., Helv. Chem. Acta 40, 2160 (1956). This halo group will appear in the final formula I product in the 5 position.

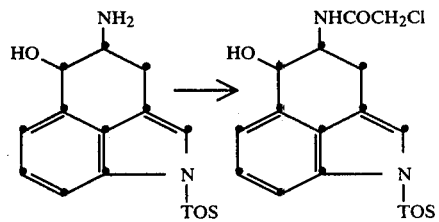

It is to be noted that carbon atoms 6a and 10a (marked by arrows in Ia) are asymmetric. This invention includes stereoisomers where these asymmetric centers are in either the R or S configurations. The compounds of this invention are understood to include the individual stereoisomers and mixtures of stereoisomers, the biological activity of which will vary. The preferred configuration for the compounds in this invention is when the groups attached to carbons 6a and 10a (nitrogen and oxygen) are in the trans relationship as noted in the experimental section and illustrated by formula Ia and its optical isomer formula Ib.

The following examples illustrate preparation of compounds of the present invention. All temperatures are in degrees Celsius.

EXAMPLE 1

Preparation of trans-4,6,6a,8,9,10a-Hexahydro-7H-indolo-[3,4-gh]-[1,4]-benzoxazine Step A Reaction Step A
trans-4-N-(γ-chloro)acetoamino-1,3,4,5-tetrahydro-1-(p-tolylsulphonyl)benz[cd]indol-5-ol To a stirred two phase system consisting of trans-4-amino-1,3,4,5-tetrahydro-1-(p-tolylsulphonyl)benz[c-d]indol-5-ol (15 gm, 0.043 m) in 1,2-dichloroethane (150 ml) and sodium hydroxide (5.4 gm) in water (75 ml) is added over a 30 minute period a solution of chloroacetylchloride (7.5 gm, 0.067 m) in 1,2 dichloroethane (50 ml). The reaction mixture is stirred for an additional 45 minutes, and then the solid is filtered to yield 16 gms of trans-4-N-(γ-chloro)acetamino-1,3,4,5-tetrahydro-(p-tolysulphonyl)benz[cd]indol-5-ol; m.p. 218°-220° C.

Step B Reaction

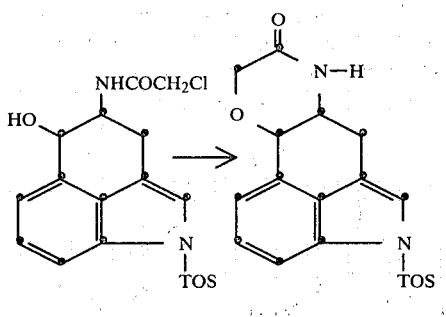

Step B:
trans-4-(p-tolylsulphonyl)-4,6,6a,8,9,10a-Hexahydro-7H-indolo-[3,4gh]-[1,4]-benzoxazin-8-one To a stirred solution of trans-4-N-(γ-chloro)acetamino-1,3,4,5-tetrahydro-1-(p-tolylsulphony)benz[cd]indol-5-ol (15 gms 0.05 m) in dimethyl formamide (24 ml) is added sodium hydride (50% in oil, 2.4 gms) in portions over 15 minutes. After stirring for ½ hour, the reaction mixture is poured into water and the resulting solid is filtered to yield 7.2 gms of trans-4-(p-tolylsulphonyl)-4,6,6a,8,9,10a-Hexahydro-7H-indolo-[3,4gh]-[1,4]-benzoxazin-8-one.

Step C Reaction

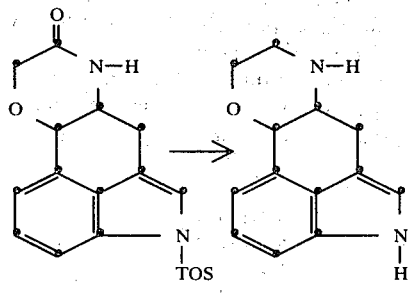

Step C: trans 4,6,6a,8,9,10a-Hexahydro-7H-indolo-[3,4-gh]-[1,4]-benzoxazine

To a stirred slurry of lithium aluminum hydride (3.0 gms) in tetrahydrofuran (200 ml) is added trans-4-(p-tolylsulphonyl)-4,6,6a,8,9,10a hexahydro-7H-indolo-[3,4-gh]-[1,4]-benzoxazin-8-one (3.0 gms) in portions over 5 minutes. The resulting mixture is refluxed for 17 hours. The cooled slurry is hydrolyzed with water (6 ml), and the organic phase is separated from the solid inorganics by filtration. The solid is rinsed with ether (3×100 ml). The organic solvents are dried over anhydrous sodium sulfate. After filtration, the solvents are removed under reduced pressure (20 mm). The resulting oil is purified by column chromatography silica; CHCl₃ (sat. with NH₄OH) to yield 700 mg of trans 4,6,6a,8,9,10a-Hexahydro-7H-indolo-[3,4 gh]-[1,4]-benzoxazine; which after recrystalization from methanol gives 540 mg (25%) m.p. 175°-177° C. with previous softening.

EXAMPLE 2

Preparation of trans-4,6,6a,8,9,10a-Hexahydro-7-methyl-7H-indolo-[3,4 gh]-[1,4]-benzoxazine Step A:
trans-4-(p-tolylsulphonyl)-4,6,6a,8,9,10a-hexahydro-7-methyl-indolo-[3,4 gh]-[1-4]-benzoxazin-8-one Sodium hydride (50% in mineral oil, 1.1 gms, 0.045 m) is added in portions to a stirred solution of trans 4-(p-tolylsulphonyl)-4,6,6a,8,9,10a hexahydro-7H-indolo-[3,4 gh]-[1,4] benzoxazin-8-one (7.0 gm, 0.018 m) in DMF (14 ml). The resulting mixture is stirred at room temperature for ½ hour. Methyl iodide (5.0 gm, 0.035 m) is added dropwise to the reaction mixture. After stirring an additional ½ hour, the reaction solution is poured into water, and the solid is removed by filtration. The tan solid is chromatographed (silica, chloroform) to give 3 gms of trans-4,6,6a,8,9,10a-Hexahydro-7-methyl-7H-indolo-[3,4 gh]-[1.4]-benzoxazine.

Step B:
trans-4,6,6a,8,9,10a-Hexahydro-7-methyl-7H-indolo-[3,4 gh]-[1,4]-benzoxazine A suspension of trans-4-(p-tolylsulphonyl)-4,6,6a,8,9,-10a-hexahydro-7-methyl-7H-indolo-[3,4 gh]-[1,4]-benzoxazin-8-one (3.0 gms; 0.008 m) and lithium aluminum hydride (3.0 gm; 0.08 m) in tetrahydrofuran (200 ml) is refluxed for 17 hours. The cooled solution is hydrolyzed with water (6 ml). The solid is filtered, and the organic solvent is dried over anhydrous sodium sulfate. After filtration, the solvent is removed under reduced pressure (20 mm). The gum is crystallized from methanol (2-5 ml) to yield 420 mg of trans-4,6,6a,8,9,10a-hexahydro-7-methyl-7H-indolo-[3,4 gh]-[1,4]-benzoxazine. This solid is purified by chromatography (silica, CHCl₃/NH₄OH) to give 330 mg of trans-4,6,6a,8,9,10a-hexahydro-7-methyl-7-H-indolo-[3,4 gh]-[1,4]-benzoxazine; m.p. 175°-177° (softening at 100°).

Preparation of hydrochloride salt:

The free base obtained from the methanol crystallization is treated with ethanolic hydrogen chloride to give 4,6,6a,8,9,10a as hydrochloride salt. After recrystalization from methanol-ether, the salt is isolated by filtration to give 350 mg m.p. darken 250° melts 295°-300°.

EXAMPLE 3

Preparation of trans-4,6,6a,8,9,10a-Hexahydro-7-ethyl-7H-indolo-[3,4 gh]-[1,4]-benzoxazine Step A:
trans-4,6,6a,8,9,10a-Hexahydro-7-ethyl-7H-indolo-[3,4 gh]-[1,4]-benzoxazine A suspension of trans-4,6,6a,8,9,10a-hexahydro-7H-indolo-[3,4 gh]-[1,4]-benzoxazine (650 mg, 0.03 m) acetaldehyde (260 mg, 0.006 m) and Pd/c (10%, 700 mg) in abs. ethanol (50 ml) is hydrogenated at room temperature for 4 hours. The catalyst is removed by filtration, and the solvent is removed under reduced pressure (20 mm). The oil is recrystallized from methanol to yield 430 mg of trans 4,6,6a,8,9,10a-hexahydro-7-ethyl-7H-indolo-[3,4 gh]-[1,4]benzoxazine, m.p. turns brown 200° melt 210°-213°.

EXAMPLE 4

Preparation of
trans-4,6,6a,8,9,10a-Hexahydro-7-n-propyl-7H-indolo[3,4 gh]-[1,4]-benzoxazine Step A:
trans-4,6,6a,8,9,10a-Hexahydro-7-n-propyl-7H-indolo-[3,4 gh]-[1,4]-benzoxazine A suspension of trans 4,6,6a,8,9,10a-hexahydro-7H-indolo-[3,4 gh]-[1,4]benzoxazine, (300 mg, 0.014 m), propionic aldehyde (300 mg, 0.005 m) and Pd/c (10%, 300 mg) in abs. ethanol (150 ml) is hydrogenated on the Hirschberg hydrogenation apparatus. After 2½ hours, the reduction mixture is removed, and the catalyst is removed by filtration. The ethanol is removed under reduced pressure (20 mm). The residue is recrystallized from methanol (5–10 ml) to yield 240 mg of trans-4,6,6a,8,9,10a-hexahydro-7-n-propyl-7H-indol-[3,4 gh]-[1,4]-benzoxazine.

EXAMPLE 5

Preparation of
trans-4,6,6a,8,9,10a-Hexahydro-7-n-butyl-7H-indolo-[3,4 gh]-[1,4]-benzoxazine Step A:
trans-4,6,6a,8,9,10a-Hexahydro-7-n-butyl-7H-indolo-[3,4 gh]-[1,4]-benzoxazine A suspension of trans-4,6,6a,8,9,10a-hexahydro-7H-indolo-[3,4 gh]-[1,4]-benzoxazine (700 mg; 0.0032 m), Pd/c (10%, 700 mg) and butrylaldehyde (500 mg, 0.006 m) in abs. ethanol (75 ml) is hydrogenated at room temperature for 8 hours. The catalyst is filtered, and the solvent is removed under reduced pressure (20 mm). The resulting oil is chromatographed (silica, chloroform, saturated with aqueous ammonia). The solid is recrystallized from hexane to yield 250 mg of trans-4,6,6a,8,9,10a-hexahydro-7-n-butyl-7H-indolo-[3,4 gh]-[1,4]-benzoxazine; m.p. softens 29°–130°, m.p. 134°–140°.

EXAMPLE 6

Preparation of
trans-4,6,6a,8,9,10a-Hexahydro-3-chloro-7H-indolo-[3,4 gh]-[1,4]-benzoxazine Step A Reaction

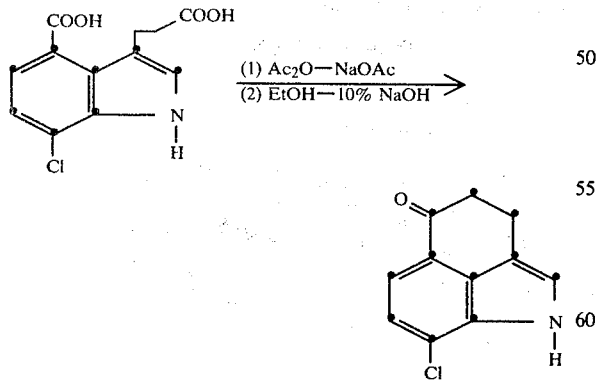

Step A: 8-Chloro-3,4-dihydrobenz[cd]-indol-5-(1H)-one

A mixture of 4-carboxy-7-chlorindole-3-propionic acid (40 g, 0.15 mole), acetic anhydride (320 ml), and anhydrous sodium acetate (3.0 g) is stirred and heated at reflux for 18 hours in the dark. The reaction mixture is cooled and then the solvent is removed under vacuum. The residue is taken up in ethanol (180 ml) and sodium hydroxide 10% (155 ml) is added slowly keeping the temperature below 45° C. After stirring for 1 hour at ambient temperature most of the ethanol is removed in vacuo and the solid that separates is recovered by filtration and dried. The yield of 8-chloro-3,4-dihydrobenz[cd]-indol-5(1H)-one is 9.1 g (30%) melting 175°–180° C. (dec). The pure compound, is crystalized from toluene and melts 185°–187° C. (dec.).

isolation of 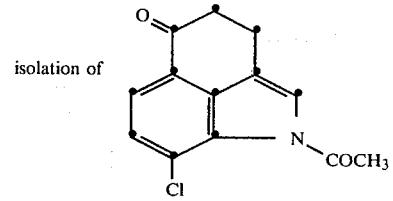

Step A-1:
1-Acetyl-8-chloro-3,4-dihydrobenz[cd]-indol-5(1H)-one

By the following procedure one can isolate the subject compound from the reaction described in Step A. After 18 hours at reflux the reaction mixture is cooled and then the solvent is removed in vacuo. To the residue is added hot ethyl acetate and the residue solidifies to a pale yellow solid. After cooling the mixture, this solid is recovered by filtration and dried to afford 1-acetyl-8-chloro-3,4-dihydrobenz[cd]-indol-5(1H)-one in 40–45% yield. The material is pure enough to use for subsequent reactions.

Step B:
1-Acetyl-4-bromo-8-chloro-3,4-dihydrobenz[cd]-indol-5(1H)-one

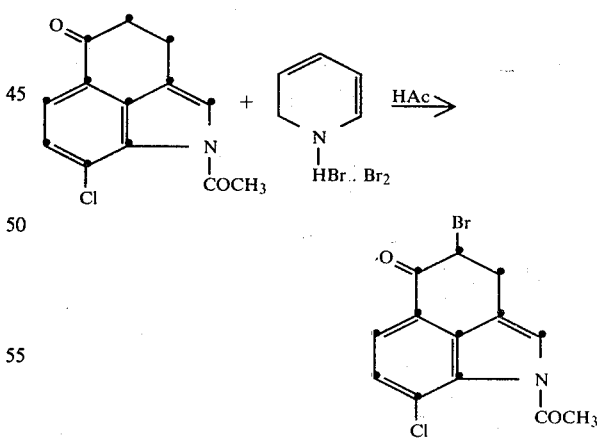

To a stirred mixture of 1-acetyl-8-chloro-3,4-dihydrobenz[cd]-indol-5(1H)-one (9.7 g, 0.04 mole) in acetic acid (80 ml.) is added in one portion pyridinium bromide perbromide (13.8 g., 0.042 mole). The stirring is continued for 3.5 hours and then water (150 ml.) is added to the reaction mixture. The dark solid that separates is recovered by filtration and dried. The crude yield is 10 g. (89%) of material that is used in the next step without further purification.

Step C:
1-Acetyl-4-azido-8-chloro-3,4-dihydrobenz[cd]-indol-5(1H)-one

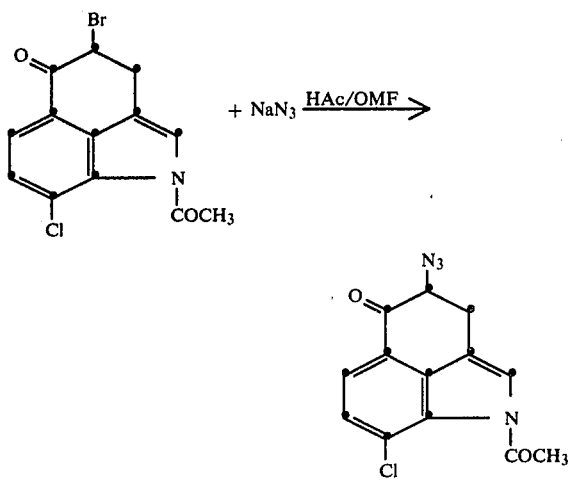

To a solution of 1-acetyl-4-bromo-8-chloro-3,4-dihydrobenz[cd]-indol-5(1H)-one (8.3 g., 0.029 mole) in dimethylformamide (70 ml.) containing 5 ml of acetic acid and cooled in an ice bath, is added a solution of sodium azide (3.8 g. in 17 ml. of $H_2O$) at such a rate that the reaction temperature does not exceed 25° C. Stirring is continued for 1.5 hours with cooling. The reaction mixture is poured into water (200 ml.) and the dark solid that separates is recovered by filtration and dried. The yield of crude 1-acetyl-4-azido-8-chloro-3,4-dihydrobenz[cd]-indol-5(1H)-one is 7.0 g. (97%).

Step D:
1-Acetyl-4-amino-8-chloro-3,4-dihydrobenz[cd]-indol-5(1H)-one-hydrochloride

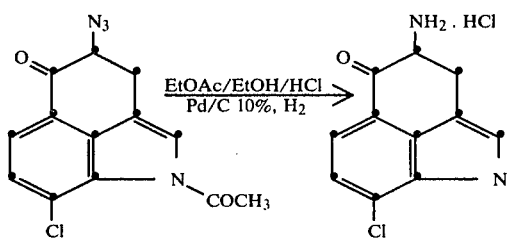

Into a stirred solution of 1-acetyl-4-azido-8-chloro-3,4-dihydrobenz[cd]-indol-5(1H)-one (3.5 g., 0.012 mole) in ethylacetate-ethanol (1:1) (200 ml.), containing 4 gm. of 6 N hydrochloric acid and 0.5 g. of 10% palladium on carbon catalyst, is bubbled a stream of hydrogen gas. After 2.5 hours the product which has separated is recovered by filtration. The yield of crude product which contains some of the catalyst is 2.6 g. (72%).

Step E:
1-Acetyl-4-chloroacetamindo-8-chloro-3,4-dihydrobenz[cd]-indol-5(1H)-one

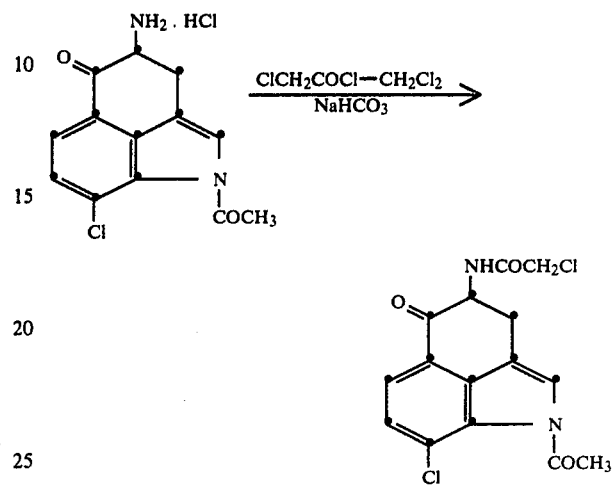

To a rapidly stirred mixture of methylenechloride (300 ml.) and 2% sodium bicarbonate (100 ml.) is added 1-acetyl-4-amino-8-chloro-3,4-dihydrobenz[cd]-indol-5(1H)-one hydrochloride (2.6 g., 0.009 mole). When the solid hydrochloride has gone into solution, chloroacetyl chloride (1.4 g., 0.012 mole) is added dropwise, and stirring is continued for 1 hour. After this time the organic layer is separated, dried, and evaporated in vacuo to afford a pale yellow solid. The yield of product is 1.6 g. (54%), m.p. 222° C. (dec.). The pure compound is crystallized from acetonitrile and melts 230°–232° C. (dec.)

Step F:
trans-1-Acetyl-4-chloroacetamido-8-chloro-1,3,4,5-tetrahydrobenz[cd]indol-5-ol

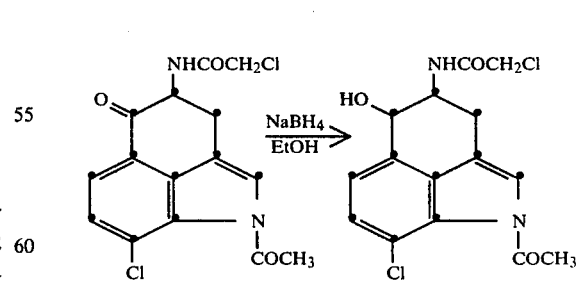

An ice cold, solution of 1-acetyl-4-chloroacetamido-8-chloro-3,4-dihydrobenz[cd]indol-5-(1H)-one in ethanol is reduced with excess sodium borohydride to the subject alcohol.

Step G:
trans-4,6,6a,8,9,10a-Hexahydro-3-chloro-7H-indolo-[3,4 gh]-[1,4]-benzoxazine-8-one

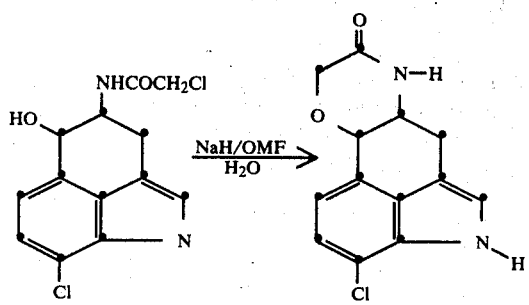

The synthesis of this compound is carried out as described in Example 1, Step B, the acetyl protecting group is hydrolized during the aqueous, work-up of the reaction mixture, to give trans-4,6,6a,8,9,10a-hexahydro-3-chloro-7H-indolo-[3,4 gh]-[1,4]-benzoxazine-8-one.

Step H:
trans-4,6,6a,8,9,10a-Hexahydro-3-chloro-7H-indolo-[3,4 gh]-[1,4]-benzoxazine

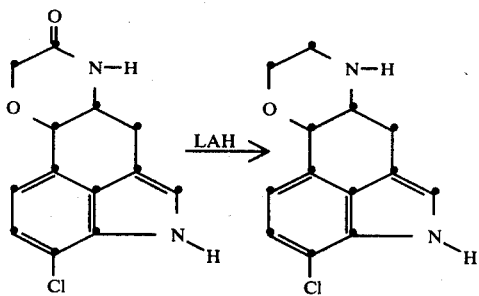

Using the method described in Example 1, Step C to reduce trans-4,6,6a,8,9,10a-hexahydro-3-chloro-7H-indolo-[3,4]-[1,4]-benzoxazine-8-one there is obtained the subject compound.

The formula I compounds of the present invention have various pharmaceutical utilities. The compounds find uses as prolactin inhibitors, antihypertensives, anti-Parkinson agents and the like.

For use in treating hypertension in humans, the formula I compound is administered orally or in suitable dosage forms at daily dosages ranging from about 10 mg to about 3,000 mg, preferably from about 20 mg to about 1,000 mg and more preferably from about 50 mg to about 500 mg.

For treating Parkinson's disease in humans, again oral or parenteral administration of the formula I compound in suitable dosage forms is used in daily dosages ranging from about 10 mg to about 1,000 mg, preferably from about 10 mg to about 500 mg and more preferable from about 20 mg to about 100 mg.

Oral administration is the preferred mode of administration in all cases. The oral dosage forms may be solid, e.g. tablets, troches, capsules, encapsulated or liquid e.g. suspension, emulsion, solution. Conventional preparation procedures are used and diluents, carrier, adjuvants are utilized in the formulations when necessary. These pharmaceutical compositions constitute another embodiment of the invention.

The antihypertensive activity of representative compounds was determined in-vivo using spontaneously hypertensive (SH) rats. A turning rat protocol was used to screen for utility as anti-Parkinson agents.

For use as prolactin inhibitors in humans, the formula I compound is administered in daily dosages ranging from about 10 mg. to about 1,000 mg., preferably 15 mg to about 500 mg and more preferably 20 mg to about 100 mg. Oral and paenteral administration in appropriate dosage forms is used. Oral administration is preferred.

What is claimed is:

1. Compounds having the formula

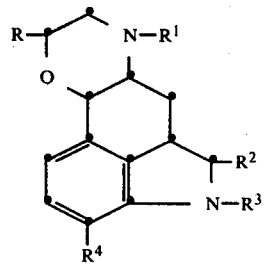

and pharmaceutically acceptable salts thereof wherein
R is H, alkyl or aryl,
$R^1$ is H, alkyl, aralkyl, cycloalkyl or alkenyl,
$R^2$ is H, halogen or alkyl,
$R^3$ is H, alkyl or aralkyl, and
$R^4$ is H, halogen, alkyl, hydroxy or alkoxy.

2. Compound of claim 1 wherein
R is H, $C_1$-$C_6$ alkyl, phenyl, substituted phenyl,
$R^1$ is H, $C_1$-$C_6$ alkyl, $C_3$-$C_4$ alkenyl $C_3$-$C_6$ cycloalkyl, phen-$C_1$-$C_4$-alkyl or substituted phen-$C_1$-$C_4$-alkyl,
$R^2$ is H, Cl, Br or $C_1$-$C_6$ alkyl,
$R^3$ is H, $C_1$-$C_6$ alkyl, phen-$C_1$-$C_4$-alkyl or substituted phen-$C_1$-$C_4$-alkyl and
$R^4$ is H, Cl, Br, $C_1$-$C_6$ alkyl, hydroxy or $C_1$-$C_4$ alkoxy.

3. Compound of claim 1 wherein
R is H, $C_1$-$C_4$ alkyl or monosubstituted phenyl wherein said substituent is halogen, $C_1$-$C_4$-alkyl or $C_1$-$C_4$ alkoxy,
$R^1$ is H, $C_1$-$C_4$ alkyl, $C_3$-$C_6$ cycloalkyl $C_3$-$C_4$ alkenyl, monosubstituted phen-$C_1$-$C_4$ alkyl wherein said substituent is halogen, $C_1$-$C_4$ alkyl or $C_1$-$C_4$ alkoxy,
$R^2$ is H, $C_1$-$C_3$ alkyl, Cl or Br,
$R^3$ is H, $C_1$-$C_3$ alkyl, monosubstituted phen-$C_1$-$C_4$-alkyl wherein said substituent is halogen, $C_1$-$C_4$ alkyl or $C_1$-$C_4$ alkoxy, and
$R^4$ is H, Cl, Br, $C_1$-$C_3$ alkoxy, hydroxy or $CH_3$.

4. Compound of claim 3 wherein $R^3$ is H.
5. Compound of claim 3 wherein $R^1$ is $C_1$-$C_4$alkyl.
6. Compounds of claim 4 wherein $R^1$ is $C_2H_5$.
7. Compounds of claim 4 wherein $R^1$ is $CH_3$.
8. Compound of claim 4 wherein $R^1$ is —$CH_2$—$CH_2$—$CH_3$.
9. Compound of claim 1 wherein each of R, $R^2$, $R^3$ and $R^4$ is H.
10. Compound of claim 9 wherein $R^1$ is $C_1$-$C_4$alkyl.
11. Compound of claim 9 wherein $R^1$ is $CH_3$, $C_2H_5$, $C_3H_7$ or $C_4H_9$.
12. Compound of claim 9 wherein $R^1$ is $CH_3$.

13. Compound of claim 9 wherein $R^1$ is $C_3H_7$.
14. Compound of claim 9 wherein $R^1$ is $C_2H_5$.
15. Compound of claim 1 wherein each of R, $R^1$, $R^2$, $R^3$ and $R^4$ is H.
16. A pharmaceutical composition for treating hypertension containing a compound of claim 1.
17. A pharmaceutical composition for treating hypertension containing a compound of claim 10.
18. A method of treating hypertension by administering an effective amount of a compound of claim 1.
19. A pharmaceutical composition for treating Parkinson's disease containing a compound of claim 1.
20. A pharmaceutical composition for treating Parkinson's disease containing a compound of claim 1 where R, $R^2$, $R^3$ and $R^4$ are each H and $R^1$ is H or $C_1$-$C_4$alkyl.
21. A method of treating Parkinson's disease by administering an effective amount of a compound of claim 1.
22. Compound of claim 4 wherein $R^1$ is $CH_2$—$CH_2$—$CH_3$.
23. Compound of claim 4 wherein $R^1$ is H.
24. Compound of claim 9 wherein $R^1$ is $-(CH_2)_3$—$CH_3$.
25. Compound of claim 9 wherein $R^1$ is H.
26. Compound of claim 9 wherein $R^1$ is $CH_3$.
27. Compound of claim 9 wherein $R^1$ is $C_2H_5$.
28. Compound of claim 9 wherein $R^1$ is $CH_2$—$CH_2$—$CH_3$.
29. A compound of claim 1 wherein R, $R^3$ and $R^4$ are each H, $R^1$ is H or $C_1$-$C_4$alkyl and $R^2$ is Cl or Br.
30. A compound of claim 1 wherein each of R, $R^3$ and $R^4$ is H, $R^1$ is $CH_3$ and $R^2$ is Br.
31. A compound of claim 1 wherein each of R, $R^3$ and $R^4$ is H, $R^1$ is $C_2H_5$ and $R^2$ is Br.
32. A compound of claim 1 wherein each of R, $R^3$ and $R^4$ is H, $R^1$ is $C_3H_7$ and $R^2$ is Br.
33. A compound of claim 1 wherein each of R, $R^3$ and $R^4$ is H, $R^1$ is H and $R^2$ is Br.
34. A compound of claim 1 wherein each of R, $R^3$ and $R^4$ is H, $R^1$ is $CH_3$ and $R^2$ is Cl.
35. A compound of claim 1 wherein each of R, $R^3$ and $R^4$ is H, $R^1$ is $C_2H_5$ and $R^2$ is Cl.
36. A compound of claim 1 wherein each of R, $R^3$ and $R^4$ is H, $R^1$ is $C_3H_7$ and $R^2$ is Cl.
37. A compound of claim 1 wherein each of R, $R^3$ and $R^4$ is H, $R^1$ is H and $R^2$ is Cl.

* * * * *

UNITED STATES PATENT AND TRADEMARK OFFICE
CERTIFICATE OF CORRECTION

PATENT NO. : 4,238,486

DATED : December 9, 1980

INVENTOR(S) : James H. Jones

It is certified that error appears in the above—identified patent and that said Letters Patent is hereby corrected as shown below:

The structural formula at column 1, lines 55-65 and at Claim 1, column 14, lines 15-25 should be:

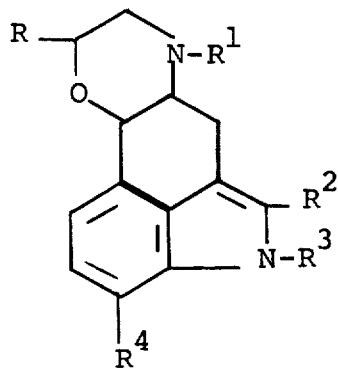

Signed and Sealed this

Twenty-fourth Day of August 1982

[SEAL]

Attest:

GERALD J. MOSSINGHOFF

Attesting Officer   Commissioner of Patents and Trademarks